United States Patent
Esquier et al.

(10) Patent No.: US 9,943,775 B2
(45) Date of Patent: Apr. 17, 2018

(54) FLEXIBLE PROCESS FOR TREATING SOLVENT, SUCH AS MONOETHYLENE GLYCOL, USED IN NATURAL GAS EXTRACTION

(71) Applicant: PROSERNAT, Paris la Defense (FR)

(72) Inventors: Jeremie Esquier, Paris (FR); Bernard Chambon, Acheres (FR); Christian Streicher, Rueil Malmaison (FR)

(73) Assignee: PROSERNAT, Paris la Defense (FR)

( * ) Notice: Subject to any disclaimer, the term of this patent is extended or adjusted under 35 U.S.C. 154(b) by 582 days.

(21) Appl. No.: 14/547,233

(22) Filed: Nov. 19, 2014

(65) Prior Publication Data
US 2015/0144477 A1    May 28, 2015

(30) Foreign Application Priority Data
Nov. 22, 2013 (FR) ..................... 13 61500

(51) Int. Cl.
*B01D 3/06* (2006.01)
*B01D 3/10* (2006.01)
(Continued)

(52) U.S. Cl.
CPC .............. *B01D 3/06* (2013.01); *B01D 3/10* (2013.01); *B01D 3/148* (2013.01); *B01D 3/34* (2013.01);
(Continued)

(58) Field of Classification Search
CPC . B01D 3/06; B01D 3/148; B01D 3/34; B01D 53/1425; C07C 29/80; C10L 3/10; C10L 3/101; C10L 3/107
See application file for complete search history.

(56) References Cited

U.S. PATENT DOCUMENTS 6,340,373 B1    1/2002    Billington
7,232,505 B2    6/2007    Laborie et al.
(Continued)

FOREIGN PATENT DOCUMENTS

EP    1415965 A1    5/2004
GB    2467169 A    7/2010
(Continued)

OTHER PUBLICATIONS

Search Report and Opinion from corresponding French Patent Application No. 13/61500 dated Jul. 9, 2014.

*Primary Examiner* — Brian A McCaig
(74) *Attorney, Agent, or Firm* — Millen, White, Zelano & Branigan, P.C.

(57) ABSTRACT

The invention concerns a flexible process for purifying a solvent which inhibits the formation of hydrates during gas processing, in particular monoethylene glycol (MEG), said solvent having a boiling point which is higher than that of water and, at least at one point in time, being mixed with water and salts, the process operating in a different manner with the same facility as a function of the quantity of salts in the MEG to be treated.

The process operates in accordance with a phase known as reclaiming (separation of salts under vacuum followed by vacuum distillation) when the salts content exceeds the precipitation threshold and if not, the process operates in a regeneration phase (absence of separation of salts and no operation under vacuum).

Advantageously, the change is made under the control of means for testing the salts.

8 Claims, 1 Drawing Sheet

(51) Int. Cl.
*B01D 3/34* (2006.01)
*C07C 29/80* (2006.01)
*B01D 53/14* (2006.01)
*B01D 3/14* (2006.01)

(52) U.S. Cl.
CPC .......... *B01D 53/1425* (2013.01); *C07C 29/80* (2013.01); *B01D 2252/2023* (2013.01)

(56) References Cited

U.S. PATENT DOCUMENTS

| | | |
|---|---|---|
| 2005/0072663 A1 | 4/2005 | Laborie et al. |
| 2012/0018293 A1 | 1/2012 | Kaasa et al. |
| 2013/0192465 A1* | 8/2013 | Trofimuk ........... B01D 19/0036 95/179 |
| 2015/0119609 A1* | 4/2015 | Deshmukh ........... B01D 9/0054 568/920 |

FOREIGN PATENT DOCUMENTS

| | | | |
|---|---|---|---|
| WO | 98/39076 A1 | 9/1998 | |
| WO | 2005092470 A1 | 10/2005 | |
| WO | 2010080038 A1 | 7/2010 | |
| WO | WO 2013/168077 A1 * | 11/2013 | ............... B01D 9/00 |

* cited by examiner

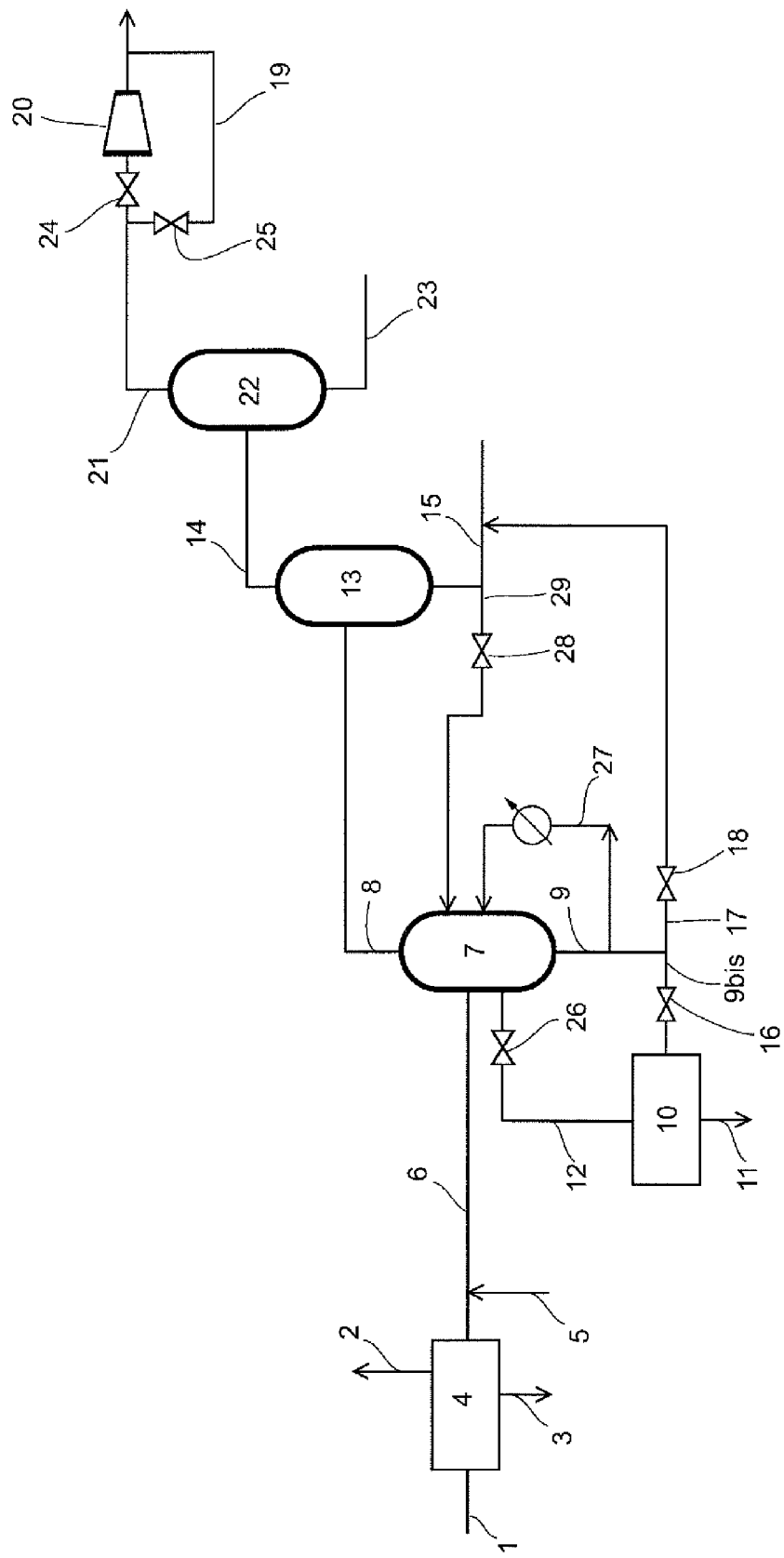

FLEXIBLE PROCESS FOR TREATING SOLVENT, SUCH AS MONOETHYLENE GLYCOL, USED IN NATURAL GAS EXTRACTION

The invention relates to a process for purifying a solvent, in particular monoethylene glycol, which is used on natural gas fields to prevent the formation of hydrates. Said solvent has a boiling point which is higher than that of water and, at least at one point in time, is mixed with water and salts.

Such hydrates are formed in the presence of water, natural gas and under conditions which favour their stability.

Their presence may become extremely hazardous to operations, since plugs can be formed in the extraction pipes or in the transport lines, which could lead to a production stoppage.

The problem is particularly acute with offshore platform operations where the gas is extracted in a relatively cold medium which is favourable to the formation of hydrates and where, moreover, gas treatments are transferred onshore, and thus the extracted gas is sent to an onshore facility and at temperatures at which the hydrates are stable.

The use of hydrate formation inhibitors such as monoethylene glycol (MEG) in order to overcome these disadvantages is known.

This solution is still expensive, due to the quantities of inhibitor which are necessary. Thus, a means for recycling the inhibitor has to be found.

A process for purifying MEG and recycling it is known, for example from patents from CCR Technologies.

Thus, patent EP 1 261 410 describes a facility and a process for purifying a hydrate formation inhibitor such as MEG. The MEG to be treated is sent to a flash drum or a column operating under vacuum in order to separate a liquid stream from the bottom of the drum (or column) comprising MEG and salts, and an essentially gaseous stream from the head of the drum (or column) comprising water and MEG. The stream of MEG and salts is partially reheated for recycling to the drum (or column), the other portion is purged, with the quantity of purge being dependent on the salt concentration. The overhead stream is distilled under vacuum to separate the water and the gases (at the head) and to recover the purified MEG (from the bottom) which is recycled to the natural gas field.

That process operates in accordance with a mode known as reclaiming.

Another mode, known as regeneration, is known for purifying MEG. In that mode, the MEG to be treated is distilled at atmospheric pressure to separate water from the column head, the stream of MEG and salts leaving from the column bottom being treated so as to separate the salts, for example by means of a vacuum drum or column.

The Applicant has observed that the reclaiming phase is energy-consuming because it is necessary to move and reheat large quantities of solvent (for example MEG). Further, fieldwork has shown that the solvent (for example MEG) may sometimes contain no formation water (water loaded with salts from the formation which is being crossed), while at other times it may contain large quantities, depending on the formations being crossed. This phenomenon is random and until now has been difficult to accommodate.

One aim of the invention is to reduce the energy consumption of the process while keeping the degree of purification high.

More precisely, the invention concerns a process for purifying a hydrate formation inhibiting solvent, said solvent having a boiling point which is higher than that of water and, at least at one point in time, being mixed with water and salts, the process comprising:

optionally, a pre-treatment of said solvent to be treated, said pre-treatment separating at least a portion of the hydrocarbons, the condensates and the gases, and said pre-treatment optionally comprising adding a chemical neutralization agent;

a reclaiming phase carried out when the quantity of salts in said solvent to be treated, which has optionally been pre-treated, reaches a precipitation threshold in the treated mixture;

said phase comprising a vacuum flash, operating at a pressure which is below atmospheric pressure and preferably in the range 0.2 to 0.5 bar absolute and at a temperature which is below the degradation temperature of the solvent, by which a stream of solvent containing salts and a vaporized stream of solvent and water are obtained, said stream of solvent and water being vacuum distilled at a pressure which is substantially equal to that prevailing in said vacuum flash in order to separate the water and recover a stream of purified solvent, the salts being separated from said stream of solvent containing the salts, then the solvent obtained being recycled to the flash;

when said quantity of salts in the treated mixture is below a precipitation threshold, stopping the reclaiming phase and carrying out a phase termed regeneration;

said regeneration phase comprising releasing the vacuum, the solvent to be treated, which has optionally been pre-treated, undergoing a flash step, operating at a pressure greater than or equal to atmospheric pressure and preferably in the range 1 to 2 bar absolute and at a temperature which is below the degradation temperature of the solvent, by which a first stream of purified solvent and a stream of solvent and water are obtained, said stream of solvent and water being distilled under a pressure substantially equal to that prevailing in said flash, the water being separated and a second stream of purified solvent being obtained, said second stream being mixed with said first stream and/or recycled to said flash.

The process is of particular application to monoethylene glycol.

The solvent to be treated (in particular MEG) is an inhibitor of hydrate formation during gas processing.

The solvent to be treated (in particular MEG) does not undergo a treatment for separating divalent salts. The divalent salts remain present in the solvent entering the flash.

The desired and obtained degree of purification of the solvent (in particular MEG) is greater than 60% by weight, preferably greater than 80% by weight.

The water obtained from the process generally contains less than 1% by weight of solvent (in particular MEG), preferably less than 0.1% by weight; it can be reused.

The invention also concerns a facility for purifying a hydrate formation inhibiting solvent, said solvent having a boiling point which is higher than that of water and, at least at one point in time, being mixed with water and salts, said facility comprising:

a flash drum 7 provided with a line 6 for introducing solvent to be treated, an outlet line 8 for a mixture of solvent and water, an outlet line 9 for a mixture of solvent and salts;

a means 10 for separating salts, provided with a line 9b is for introducing a mixture of solvent and salts, said line 9b is comprising a valve 16, the means 10 also being provided with an outlet line 11 for the separated salts and an outlet line 12 for the solvent separated from the salts, said line 12 being connected to the flash drum 7 and provided with a valve 26;

a distillation column 13 which can operate under vacuum, provided with a line 6 for introducing said mixture of solvent and water, an outlet line 15 for purified solvent at the column bottom, and an outlet line 14 for water and gas located at the column head;

a line 17 provided with a valve 18 connecting said line 9 to the purified solvent outlet line 15;

a vacuum-producing system 20 which can deliver a reduced pressure in the distillation column and the flash drum, a line 19 for bypassing said system and valves 24 and 25 at said system and said bypass line respectively;

a line 29 provided with a valve 28, connecting the line 15 to the flash drum 7, and said facility operating in accordance with 2 phases depending on the salt content of the solvent delivered via the test means:

in one of the phases, the valves 18, 25 and 28 are closed, the valves 26, 16 and 24 are open and said vacuum-producing system supplies a reduced pressure;

in the other phase, the valves 16, 26 and 24 are closed, the valves 18, 25 and 28 are open and said vacuum-producing system is stopped.

Preferably, upstream of the flash drum, the facility comprises a pre-treatment comprising a means 4 for separating hydrocarbons, condensates and gases and the line 6 for recovering the pre-treated solvent.

Preferably, the facility further comprises a line 5 connected to the line 6 for introducing a chemical agent.

Advantageously, the facility further comprises a line 14 for introducing water and gas into a means 22 for separating gases from said water, said means comprising a water outlet line 23 and a gas outlet line 21, said line 21 being connected to the vacuum-producing system 20 (for example a compressor).

The facility is of particular application when the solvent is monoethylene glycol.

The invention will now be described with reference to the layout of FIG. 1: the solvent is MEG, but the FIGURE can be described with any other solvent as defined in the invention; "MEG" can be replaced by "solvent".

Upstream of the process proper, a pre-treatment is advantageously carried out.

The MEG to be treated (supplied via the line 1) is generally separated from gases (leaving via the line 2) and condensates and hydrocarbons (leaving via the line 3) in a drum 4. Traces or small quantities of hydrocarbons, condensates or gas may remain, depending on the intensity of separation.

The MEG obtained contains water and salts. It is optionally neutralized, for example using sodium hydroxide (supplied via the line 5).

Preferably, the MEG is separated from the gases, condensates and hydrocarbons, and then is neutralized.

The MEG is also preheated.

The MEG to be treated contains a high proportion of water (in general 10% to 95% by weight), a quantity of salts which may be high (for example 0 g/l to 90 g/l or higher), the remainder being essentially MEG.

It will be noted that the MEG to be treated does not undergo separation of the divalent salts. The divalent salts remain present in the MEG entering the flash drum, described below.

The operator has at his disposal a means for testing the quantity of salts in the MEG to be treated.

It may be a manual means (tapping off a sample and testing) or an automated means (in-line measurement, or taking a sample followed by testing and controlling).

This means is specific to the MEG to be treated or to MEG obtained after separation of the gases and condensates or to neutralized MEG, preferably to the neutralized MEG.

When the quantity of salts is higher than a threshold for precipitation of said salts in the incoming mixture (to be treated or pre-treated), the process operates in a reclaiming phase, which is described below.

The MEG to be treated, containing water and salts, preferably obtained from a pre-treatment, preferably including neutralization, is sent to a separation drum 7 via the line 6. A mixture of MEG and salts leaves the bottom of the drum. A mixture of MEG and water leaves the head of the drum (line 8).

This separation of the salts is the first step in the phase known as reclaiming.

The separation step is operated at a pressure below atmospheric pressure, preferably in the range 0.2 to 0.5 bar absolute, and at a temperature which is substantially equal to the boiling point of monoethylene glycol (or more generally the solvent).

In order to obtain the desired temperature, heat exchangers may be provided, as well as a reboiler system 27 on the (conventional) drum. This system has a high energy consumption, since large quantities of MEG and water are reheated and vaporized.

The mixture of MEG and salts is withdrawn from the bottom of the drum (via the line 9), and then the salts are separated by appropriate means (means 10 for separating salts). As an example, it is possible to use a sedimentation drum associated with a centrifuge; any means known to the skilled person would be suitable. The salts leave the process (via the line 11) and the MEG obtained (generally free of salts) is recycled to the flash (via the line 12), after optional reheating.

The MEG, mixed with water (from line 8), is distilled in a vacuum distillation column 13. The water is separated overhead (leaving via the line 14) and the purified MEG is recovered from the column bottom (via the line 15). It can then be recycled for field production.

This distillation corresponds to the second reclaiming step.

The vacuum is produced by means of a vacuum-producing system 20 (such as a compressor) located on the line 21 for withdrawing gases obtained from the vacuum distillation, said gases having been separated from the water (leaving via the line 23) via a separation means 22 located on the line 14 for evacuating effluent from the head of the distillation column 13 which operates under vacuum.

In accordance with the invention, when the quantity of salts in the MEG to be treated (or pre-treated) is below the threshold for precipitation of said salts, the same facility is operated in a different manner. The reclaiming phase is stopped and a phase termed regeneration is carried out.

To change from the reclaiming phase to the regeneration phase, a valve 16 is provided in the facility on the line 9 which closes off access to the means 10 for separating salts; a line 17 being provided which connects the bottom of the drum 7 to the line 15 for withdrawing purified MEG, said line 17 is provided with a valve 18. The facility is also provided with a line 19 for bypassing the vacuum-producing system 20.

The process no longer operates under vacuum, as the vacuum-producing system has been bypassed (valve 24 is closed). The pressure is established at a pressure which is greater than or equal to atmospheric pressure and preferably is in the range 1 to 2 bar absolute.

The MEG entering the flash drum is separated, at a temperature below the MEG degradation temperature (or more generally the solvent), into a first stream of purified monoethylene glycol and a stream of monoethylene glycol and water. Said first stream leaves from the drum bottom and, with the valve 16 being closed, and the valve 18 being open, it is transferred via the line 17 to the line 15.

Said stream of monoethylene glycol and water is distilled to separate the water and the remaining gases (leaving via the line 14) and to recover a second stream of purified monoethylene glycol leaving via the line 15.

In one case, said first and second streams are mixed and evacuated for re-use as a solvent. The proportion of the streams will depend on the operating conditions, the quality of the flash separation and the desired degree of purification.

In another case, said second stream is optionally recycled to the flash step (drum 7) via the line 29. The valve 28 allows or prohibits this recycling. This valve is closed in the reclaiming phase.

Preferably, a portion of said second stream is mixed with said first stream. The mixture is reused as a solvent. The other portion of said second stream is recycled to the flash step (drum 7).

The desired and obtained degree of purification of the MEG is more than 60% by weight, preferably more than 80% by weight.

The water obtained from the process generally contains less than 1% by weight of MEG and preferably less than 0.1% by weight; it can be reused.

It is apparent that this process can save large amounts of energy (savings in the reboiler system 27 of the separation drum 7 and in the vacuum-producing system 20 (such as a compressor) and allows for great flexibility in operation; changing from one phase to the other is kept very simple.

One advantage is that it is possible to operate manually or automatically, with suitable control of the valves depending on the quantities of salts.

This process can be used to produce an excellent recovery rate for the solvent (in particular MEG) which is more than 99.5%; MEG losses are thus very minimal.

By way of example, in the case in which the MEG to be treated contains 70% by weight of MEG and 30% by weight of water, the purified MEG contains 80% by weight of MEG and 20% by weight of water. In the regeneration phase, the process consumes 30% of the energy consumed by the process in the reclaiming phase, which means that a significant amount of energy is saved.

The process and facility described for MEG are suitable for the other solvents used in the treatment of gases, such as alkanolamines, for example monoethanolamine (MEA), diethanolamine (DEA), methyldiethanolamine (MDEA), etc.

BRIEF DESCRIPTION OF THE DRAWING

FIG. 1—A schematic diagram.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French Application No. FR 13/61,500, filed Nov. 22, 2013 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for purifying a hydrate formation inhibiting solvent, said solvent having a boiling point which is higher than that of water and, at least at one point in time, being mixed with water and salts, the process comprising:
    optionally, a pre-treatment of said solvent to be treated, said pre-treatment separating at least a portion of the hydrocarbons, condensates, and gases, and said pre-treatment optionally comprising adding a chemical neutralization agent;
    determining whether the quantity of salts in a treated mixture is above, equal to, or below a precipitation threshold;
    a reclaiming phase carried out when the quantity of salts in said solvent, which has optionally been pre-treated, is equal to or greater than the precipitation threshold in the treated mixture;
    said phase comprising a vacuum flash, operating at a pressure which is below atmospheric pressure and at a temperature which is below the degradation temperature of the solvent, by which a stream of solvent containing salts and a vaporized stream of solvent and water are obtained, said stream of solvent and water being vacuum distilled at a pressure which is substantially equal to that prevailing in said vacuum flash in order to separate the water and recover a stream of purified solvent, the salts being separated from said stream of solvent containing the salts, then the solvent obtained being recycled to the flash;
    wherein when said quantity of salts in the treated mixture is below a precipitation threshold, stopping the reclaiming phase and carrying out a phase termed regeneration;
    said regeneration phase comprising releasing the vacuum, the solvent to be treated, which has optionally been pre-treated, undergoing a flash step, operating at a pressure greater than or equal to atmospheric pressure and at a temperature which is below the degradation temperature of the solvent, by which a first stream of purified solvent and a stream of solvent and water are obtained, said stream of solvent and water being distilled under a pressure substantially equal to that prevailing in said flash, the water being separated and a second stream of purified solvent being obtained, said second stream being mixed with said first stream and/or recycled to said flash.

2. The process according to claim 1, in which the solvent is monoethylene glycol.

3. The process according to claim 1, in which the solvent is an alkanolamine.

4. The process according to claim 3, in which the solvent is selected from the group formed by monoethanolamine (MEA), diethanolamine (DEA) and methyldiethanolamine (MDEA).

5. The process according to claim 1, in which the solvent to be treated does not undergo a treatment for separating divalent salts.

6. The process of claim 1, wherein the pressure of the vacuum flash is in the range of 0.2 to 0.5 bar absolute.

7. The process of claim 1, wherein the pressure of the regeneration phase is in the range 1 to 2 bar absolute.

8. A process for purifying a hydrate formation inhibiting solvent, said solvent having a boiling point which is higher than that of water and, at least at one point in time, being mixed with water and salts, the process comprising:

optionally, a pre-treatment of said solvent to be treated, said pre-treatment separating at least a portion of the hydrocarbons, condensates, and gases, and said pre-treatment optionally comprising adding a chemical neutralization agent;

a reclaiming phase carried out when the quantity of salts in said solvent, which has optionally been pre-treated, reaches a precipitation threshold in the treated mixture;

said phase comprising a vacuum flash, operating at a pressure which is below atmospheric pressure and at a temperature which is below the degradation temperature of the solvent, by which a stream of solvent containing salts and a vaporized stream of solvent and water are obtained, said stream of solvent and water being vacuum distilled at a pressure which is substantially equal to that prevailing in said vacuum flash in order to separate the water and recover a stream of purified solvent, the salts being separated from said stream of solvent containing the salts, then the solvent obtained being recycled to the flash;

wherein when said quantity of salts in the treated mixture is below a precipitation threshold, stopping the reclaiming phase and carrying out a phase termed regeneration;

said regeneration phase comprising releasing the vacuum, the solvent to be treated, which has optionally been pre-treated, undergoing a flash step, operating at a pressure greater than or equal to atmospheric pressure and at a temperature which is below the degradation temperature of the solvent, by which a first stream of purified solvent and a stream of solvent and water are obtained, said stream of solvent and water being distilled under a pressure substantially equal to that prevailing in said flash, the water being separated and a second stream of purified solvent being obtained, said second stream being mixed with said first stream and/or recycled to said flash, and wherein said process includes at least one regeneration phase and at least one reclaiming phase.

* * * * *